(12) United States Patent
Chevalier et al.

(10) Patent No.: US 6,389,908 B1
(45) Date of Patent: *May 21, 2002

(54) METHOD AND DEVICE FOR CHARACTERIZING OIL BOREHOLE EFFLUENTS

(75) Inventors: Philippe Chevalier, Verrieres le Buisson; Gerard Segeral, Gif sur Yvette, both of (FR)

(73) Assignee: Schlumberger Technology Corporation, Ridgefield, CO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,873

(22) Filed: May 14, 1998

(30) Foreign Application Priority Data

May 30, 1997 (FR) .............................. 97 06648

(51) Int. Cl.$^7$ ................................ G01F 1/44
(52) U.S. Cl. ................................. 73/861.63
(58) Field of Search ............. 73/861.63, 861.04, 73/61.1, 19.12

(56) References Cited

U.S. PATENT DOCUMENTS

| | | | |
|---|---|---|---|
| 4,558,219 A | * 12/1985 | LeBlanc et al. | ............ 250/260 |
| 4,788,852 A | * 12/1988 | Martin et al. | ............ 73/61.1 R |
| 5,361,632 A | * 11/1994 | Magnani | ............ 73/153 |
| 5,841,020 A | * 11/1998 | Guelich | ............ 73/19.12 |

FOREIGN PATENT DOCUMENTS

| | | | |
|---|---|---|---|
| EP | 0 236 623 | 9/1987 | ......... G01N/23/06 |
| WO | WO 94/25859 | 11/1994 | ......... G01N/23/12 |

OTHER PUBLICATIONS

J. Williams, *Status of Multiphase Flow Measurement Research*, SPE 28515, SPE Annual Technical Conference, New Orleans (Sep. 25–28, 1994).

A. M. Scheers and W. F. J. Slijkerman, *Multiphase Flow Measurement Using Multiple Energy Gamma Ray Absorption* (MEGRA) Composition Measurement, SPE 36593 (Oct. 6, 1996).

Database WPI, Week 8930, Derwent Publications Ltd., London, GB; AN89–216574, XP002057575 (Matsushita Elec Ind Co Ltd), Jun. 16, 1989.

* cited by examiner

*Primary Examiner*—Benjamin R. Fuller
*Assistant Examiner*—Jewel V. Thompson
(74) *Attorney, Agent, or Firm*—William B. Batzer

(57) ABSTRACT

The invention relates to a method of characterizing an oil borehole effluent, formed by a multiphase fluid mixture typically containing water, oil, and gas. According to the invention, a gadolinium 153 source is used to emit gamma rays at a first energy level of about 100 keV and at a second energy level of about 40 keV, and the attenuation of the gamma rays at these two energy levels is measured after the rays have passed through the effluent.

4 Claims, 3 Drawing Sheets

METHOD AND DEVICE FOR CHARACTERIZING OIL BOREHOLE EFFLUENTS

BACKGROUND OF THE INVENTION

The invention relates to measurements relating to the composition of oil well effluents, constituted by multiphase fluids typically comprising three phases: two liquid phases, namely crude oil and water, plus a hydrocarbon gas phase, and more particularly to measurements of gamma ray attenuation by the fluid. The invention also relates to the association of such measurements with flow rate measurements in order to determine the flow rates of the various phases.

In the oil industry, the traditional practice is to separate the effluent into its component phases and to perform measurements on the phases separated in this way. However that technique requires separators to be installed on site, which separators are bulky and expensive items of equipment, and when testing wells, it also requires additional pipes to be put into place.

Numerous proposals have been put forward for developing techniques that would make it possible to avoid using such separators. A description of these developments is to be found in SPE publication 28515 (SPE Annual Technical Conference, New Orleans, Sep. 25–28, 1994) by J. Williams, "Status of multiphase flow measurement research".

Amongst such proposals, U.S. Pat. No. 4,788,852 describes apparatus including a device for measuring gamma ray attenuation, that device being associated with a Venturi total flow rate sensor and being situated at the constriction of the Venturi. Apparatus of that type is also described in patent application WO 94/25859 and in SPE publication 36593 dated Oct. 6, 1996, "Multiphase flow measurement using multiple energy gamma ray absorption (MEGRA) composition measurement" by A. M. Scheers and W. F. J. Slijkerman.

SUMMARY OF THE INVENTION

The invention seeks to provide such gamma ray attenuation measurements in an advantageous manner, that is particularly well adapted for being associated with flow rate measurements using the Venturi effect.

In one aspect, the invention provides a method of characterizing an oil borehole effluent, formed by a multiphase fluid mixture which typically comprises water, oil, and gas, comprising the steps of emitting gamma rays at a first energy level of about 100 keV and at a second energy level of about 40 keV, and measuring the attenuation of the gamma rays at these two energy levels after transmission through the effluent.

BRIEF DESCRIPTION OF THE DRAWINGS

The invention will be well understood on reading the following description given with reference to the accompanying drawings. The list of drawings is as follows.

DESCRIPTION OF THE PREFERRED EMBODIMENTS

Figure 1:
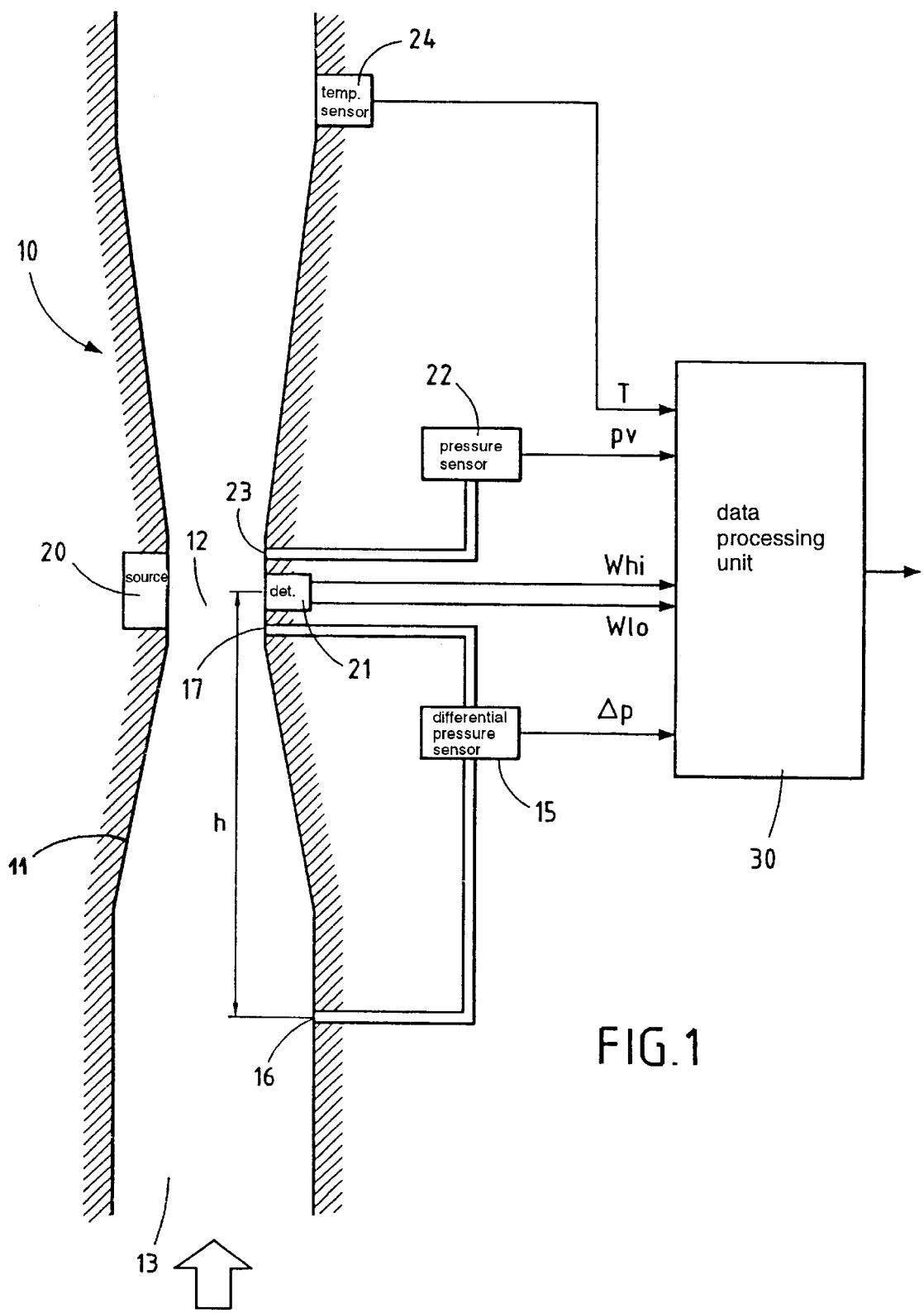
FIG. 1 is a diagrammatic view of a measurement device for characterizing an oil well effluent, including a Venturi section and a device for measuring gamma ray attenuation.

FIG. 1 shows in highly diagrammatic manner a flow meter device adapted to oil well effluent.

The device comprises a pipe section 10 comprising a converging Venturi 11 whose narrowest portion 12 is referred to as the throat. In the example shown, the section of the pipe 10 is disposed vertically and the effluent flows upwards, as symbolized by arrow F.

The constriction of the flow section in the Venturi induces a pressure drop $\Delta p$ between the level 13 situated upstream from the Venturi at the inlet to the measurement section and the throat 12. This pressure drop is associated with the total mass flow rate Q and with the density $\rho_m$ by the following relationship:

$$\Delta p = \frac{K \cdot Q^2}{\rho_m} + \rho_m g h_V \qquad (1)$$

where g is the acceleration due to gravity, $h_V$ is the distance between the upstream level 13 and the throat 12, and K is a constant associated essentially with the geometry of the Venturi, and which is given by:

$$K = \frac{1 - \beta^4}{2C^2 A^2}$$

where $\beta$ is the constriction ratio of the Venturi, i.e. the ratio between the diameter of the throat and the upstream diameter of the Venturi, C is the discharge coefficient, and A is the section of the throat. The term $\rho_m \cdot g \cdot h_V$ s generally small or negligible. By writing $\Delta p^* = \Delta p - \rho_m \cdot g \cdot h_V$, relationship (1) becomes:

$$Q = k(\Delta p^* \cdot \rho_m)^{1/2} \qquad (2)$$

where $k = K^{-1/2}$

The density $\rho_m$ is measured at the throat of the Venturi. This is relevant to the validity of relationship (2) for the following reason. The acceleration, and consequently the pressure drop, to which the fluid in the Venturi is subject takes place in privileged manner in the region close to the throat, because velocity, which is proportional to the square of the diameter, increases considerably in this region. Relationship (2) normally assumes a single phase fluid. It remains suitably applicable to a multiphase fluid providing density $\rho_m$ is measured at the throat. This is particularly true with increasing Venturi effect, and for this reason, an appropriate value for the constriction ratio is $\beta = 0.5$. With a pipe having a diameter of 10 cm, the diameter in the throat is then 5 cm.

The discharge coefficient C is approximately 1. It depends to a small extent and in predictable manner on the properties of the fluid. Traditionally, this corrective effect is taken into account by the Reynolds number.

The pressure drop $\Delta p$ is measured by means of a differential pressure sensor 15 connected to two pressure takeoffs 16 and 17 opening out into the measurement section respectively at the upstream level 13 and in the throat 12 of the Venturi. In a variant, the measurement may also be performed by means of two absolute pressure sensors connected to the pressure takeoffs 16 and 17, respectively.

The density $\rho_m$ of the fluid mixture is determined by means of a sensor which measures the attenuation of gamma rays, by using a source 20 and a detector 21 placed on opposite sides of the Venturi throat 12. The throat is provided with "windows" of material of low photon absorption at the energies under consideration. The source 20 produces gamma rays at two different energy levels, referred to below as the "high energy" level and as the "low energy" level. The detector 21 which comprises in conventional manner a scintillator crystal such as NaI and a photomultiplier produces two series of signals $W_{hi}$ and $W_{lo}$ referred to as count rates, representative of the numbers of photons detected per sampling period in the energy ranges bracketing the above-mentioned levels respectively.

These energy levels are such that the high energy count rate $W_{hi}$ is essentially sensitive to the density $\rho_m$ of the fluid mixture, while the low energy count rate $W_{lo}$ is also sensitive to the composition thereof, thus making it possible to determine the water content of the liquid phase.

It is suitable for the high energy level to lie in a range 85 keV to 150 keV. For characterizing oil effluent, this energy range presents the remarkable property whereby the mass attenuation coefficient of gamma rays therein is substantially the same for water, for sodium chloride, and for oil, being about 0.17 cm$^2$/g. This means that the high energy attenuation makes it possible to determine the density $\rho_m$ of the fluid mixture without that requiring auxiliary measurements to be performed to determine the properties of the individual phases of the fluid mixture (attenuation coefficients and densities).

The attenuation measured by the detector 21 is expressed by the following relationship:

$$A = D_V \cdot v_m \cdot \rho_m \quad (3)$$

where $D_V$ is the distance travelled through the fluid, i.e. in this case the diameter of the Venturi throat, and $v_m$ is the mass attenuation coefficient of the fluid mixture.

Since the mass attenuation coefficients of water and oil in the energy range above are substantially identical, and since the contribution of the gas is negligible because of its very low density, the mass attenuation coefficient $\mu_m$, and thus the product $D_V \cdot v_m$ that appears in equation (3) can be considered as being substantially constant and independent of the densities $\rho_o$ and $\rho_w$ of the oil and water phases.

Under such conditions, the high energy attenuation $A_{hi}$ is a very advantageous indicator of the density $\rho_m$ of the mixture.

A material that is suitable for producing high energy gamma rays in the energy range under consideration and low energy rays is gadolinium 153. This radioisotope has an emission line at an energy that is approximately 100 keV and that is entirely suitable for use as the high energy source. Gadolinium 153 also has an emission line at about 40 keV, which is suitable for the low energy level that is used to determine water content. This level provides good contrast between water and oil, since the attenuation coefficients at this level are significantly different, typical values being 0.228 cm$^2$/g for oil and 0.291 cm$^2$/g for sea water. It is also well separated from the high energy level and well above the noise level of the detector.

On the topic of the above-described gamma ray attenuation sensor, it should be observed that uses can be envisaged therefor other than those described above. The sensor may be used on its own and thus only provide water content information, in which case the sensor may be mounted in a straight section of pipe, or it may be combined with a flow rate sensor of a type other than a Venturi sensor. As an example of such sensors, mention can be made in particular of devices in which, as for a Venturi, a change of flow velocity is induced and the resulting pressure drop is measured (perforated plates).

FIG. 1 also shows a pressure sensor 22 connected to a pressure takeoff 23 opening out into the throat 12 of the Venturi, which sensor produces signals representative of the pressure $p_V$ in the throat of the Venturi, and a temperature sensor 24 producing signals T representative of the temperature of the fluid mixture. The data $p_V$ and T is used in particular for deriving gas density $\rho_g$ under line conditions and gas flow rate $q_g$ under normal conditions of pressure and temperature from the value for the flow rate under line conditions, determined in a manner described below. In this respect, it is preferable for the pressure to be measured at the throat of the Venturi. In contrast, it does not matter where temperature is measured.

Finally, a block 30 represents a unit for acquiring and processing data, which unit receives the signals coming from the above-mentioned sensors.

Figure 2:
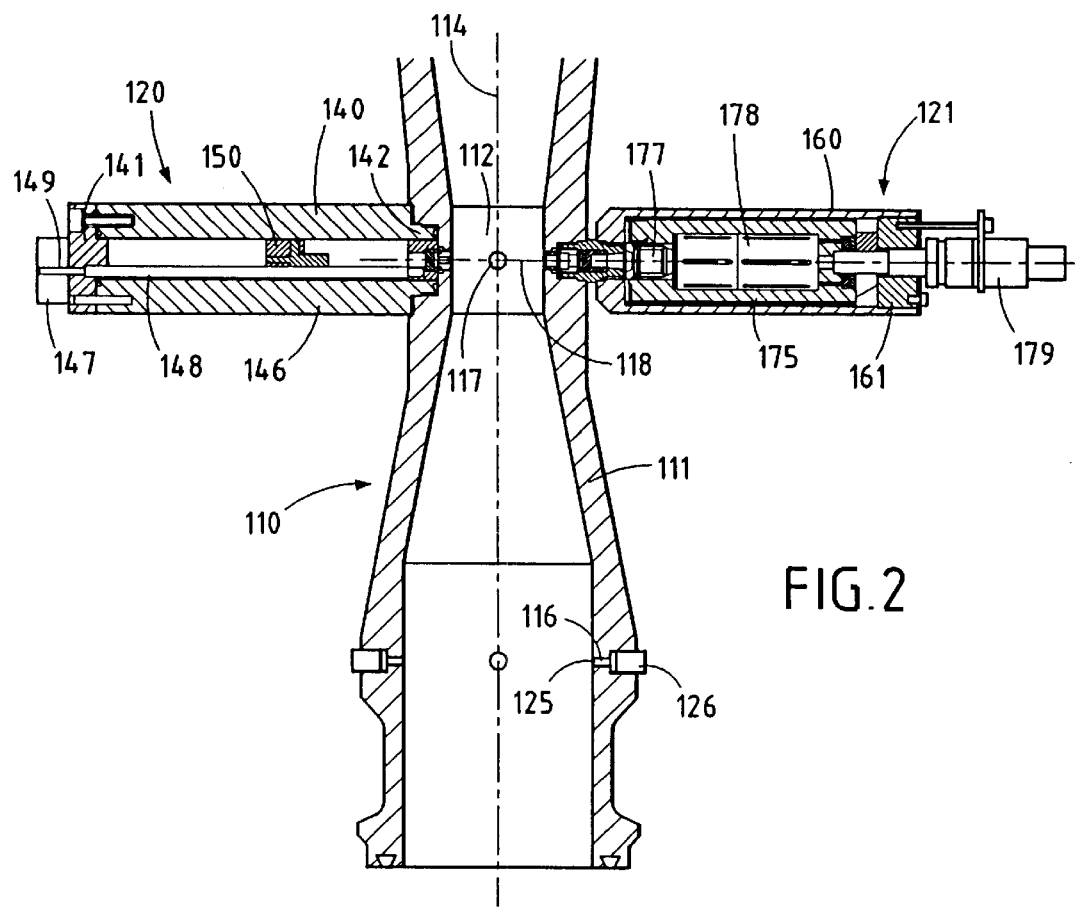
FIG. 2 is a longitudinal section through an embodiment of the FIG. 1 device.
Figure 3:
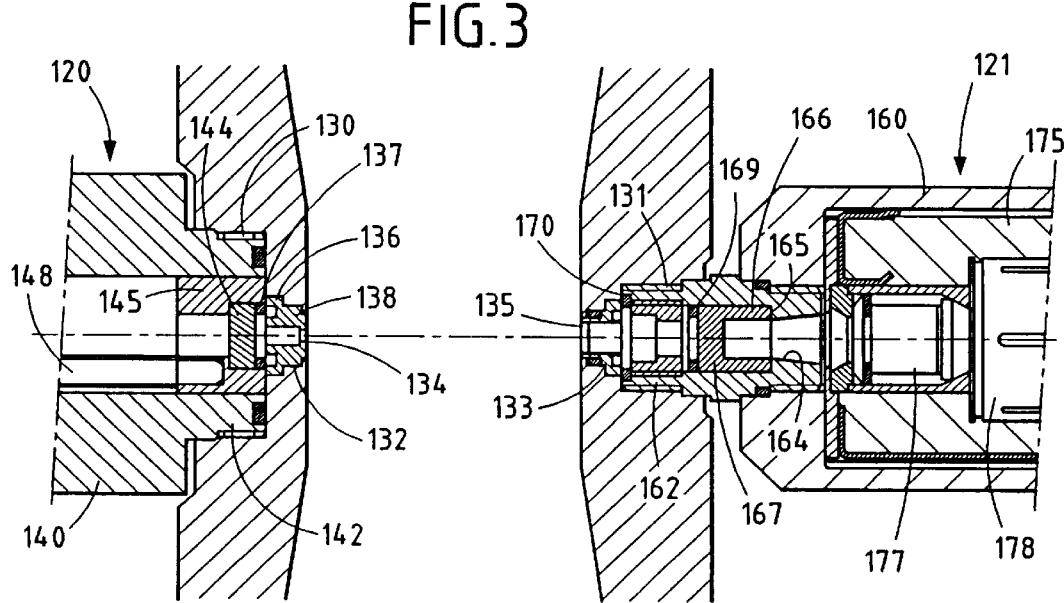
FIG. 3 is a detail view showing a portion of the device shown in FIG. 2, but on a larger scale.

Description with Reference to FIGS. 2 and 3

FIG. 2 is a section through an embodiment of the Venturi section 10 shown diagrammatically in FIG. 1, and FIG. 3 shows in greater detail how the elements 20 and 21 of the gamma attenuation measuring device are assembled at the throat of the Venturi. Elements corresponding to elements of FIG. 1 are designated herein with the same reference numeral plus 100. The Venturi section 110 thus includes a converging portion 111 whose throat 112 is the narrowest portion thereof.

In FIG. 2, there can be seen pressure takeoff orifices 116 disposed at the upstream level 113 of the Venturi. Other pressure takeoff orifices 117 are to be found at the level of the throat 112. Each of these orifices is provided with a bore 125 opening out into the throat 112, and with a tapped hole 126 of larger diameter in which it is possible to fix the endpiece of a duct (not shown), in order to put the flow into communication, as appropriate, with a differential pressure sensor or with an absolute pressure sensor such as the sensors 15, 22 mentioned with reference to FIG. 1. The number of orifices is optional. FIG. 2 shows two pairs of orifices 116 disposed at 90°, however an appropriate measurement can be obtained with a single orifice 116.

FIG. 2 shows the gamma ray attenuation measurement device constituted by a source block 120 and a detector block 121, both assembled to the Venturi section. These elements have a longitudinal axis 118 disposed perpendicularly to the axis 114 of the Venturi section at its throat 112 and they are shown in longitudinal section in FIG. 3. FIG. 3 shows in greater detail firstly the housings 130 and 131 opening out into the outside wall of the Venturi and provided with threads to enable the source block 120 and the detector block 121 to be screwed respectively thereto, and also showing housing 132 and 133 opening out into the inside wall of the Venturi and receiving the "windows" (pieces of material presenting low gamma ray attenuation) 134 and 135, together with the associated elements. Each window is held in place by a tubular element 136 screwed into a larger diameter threaded portion 137 of the corresponding housing, together with a gasket 138 held against a shoulder in the housing. This arrangement of the windows provides a sealing barrier and enables the source block 120 and the detector block 121 to be implemented in the form of removable elements that can be dismounted in complete safety. In an appropriate embodiment, the windows 134 and 135 are made of beryllium, a material that presents low gamma ray attenuation at the energies under consideration, coated with a protective layer of boron hydride, a material which is highly resistant to corrosion and wear and which also has low gamma ray attenuation. It should be observed that the windows 134 and 135 which are described above as being distinct elements could also be implemented in the form of diametrically opposite distinct portions of a single annularly-shaped part housed in a recess of complementary shape formed inside the Venturi section. Under such circumstances, the gasket would naturally have the appropriate annular shape.

The source block 120 as shown in FIG. 2 is adapted to using a radioisotope having a short lifetime, such as the above-mentioned gadolinium 153 whose half-life is about 7 months, since it enables declining activity of the source to be compensated by reducing the distance of the source from the throat 112 of the Venturi section.

In the embodiment shown, the source block comprises a body 140 of tubular shape having a central bore that is closed by a plug 141 at its end remote from the Venturi section 110, and provided at its other end with a portion 14 of smaller diameter suitable for being screwed into the above-mentioned housing 130, said portion 142 having an O-ring 143 on its front face. The central bore is closed at its end at the portion 142 by a path 144 of material of low gamma ray attenuation, and that bears against a ring 145. The source proper 146, preferably a gadolinium 153 source having activity of 100 millicuries, for example, is centered in the central bore, and is displaceable along the longitudinal axis 118 by means of an adjustment knob 147. The knob 147 is mounted at the end of a wormscrew 148 that is eccentric relative to the axis 118. The screw 148 is supported at one end by the ring 145 which is provided with a recess for this purpose, and it is fixed at its other end to a rod 149 passing through the plug 141, and it forms the shaft of the adjustment knob 147. The source 148 is fixed to a source carrier 150 whose shape on one side matches the inside wall of the tubular body 140 so as to be slidable inside the tubular body, and which is provided with teeth adapted to engage with the wormscrew 148. It is thus possible to move the source 146 in translation inside the tubular body 140, in particular to bring it closer to the Venturi section, by turning the adjustment knob 147.

This maneuver can serve to compensate for the source's drop in activity over time, in an embodiment where the source is gadolinium 153. Another advantage of this arrangement, regardless of the type of source used, is that it makes it possible to adapt the photon flux emitted by the source 146 to the nature, and thus to the attenuation characteristics, of the multiphase fluid flowing through the Venturi section.

It should be observed that any displacement of the source 146 requires a new measurement of the "empty" count rate $W_{hi,0}$ and $W_{lo,0}$ since the photon flux reaching the detector is modified by displacing the source.

Like the source block 120, the detector block 121 includes a generally tubular body 160 closed at one end by a plug 161 and including at its other end, for assembly to the Venturi section, a portion 162 of smaller outside diameter that is designed to be screwed into the above-mentioned housing 131. A bore 164 passes through portion 162 and has two portions of different diameters so as to form a shoulder 165 against which there bears on one side a ring 167 of a material of low photon absorption at the energies emitted by source 146, the ring 167 being in abutment on the other side against the shoulder of housing 131.

A box 175 of cylindrical outside shape is located in the tubular body 160, said box being axially slidable relative to the body 160, a helical spring being mounted between box 175 and a recess formed in plug 161. The box contains a detector unit 177, 178 comprising, as mentioned above, a scintillator crystal, e.g. of sodium iodide, together with a photomultiplier. The above-mentioned circuit for processing pulses (not shown) is integrated in this detector unit and is thus placed inside the box 175. Conductors, generally referred to as numeral 179, connect the detector unit to an external power supply and the detector unit 177, 178 to the data processing unit 30.

Figure 4:
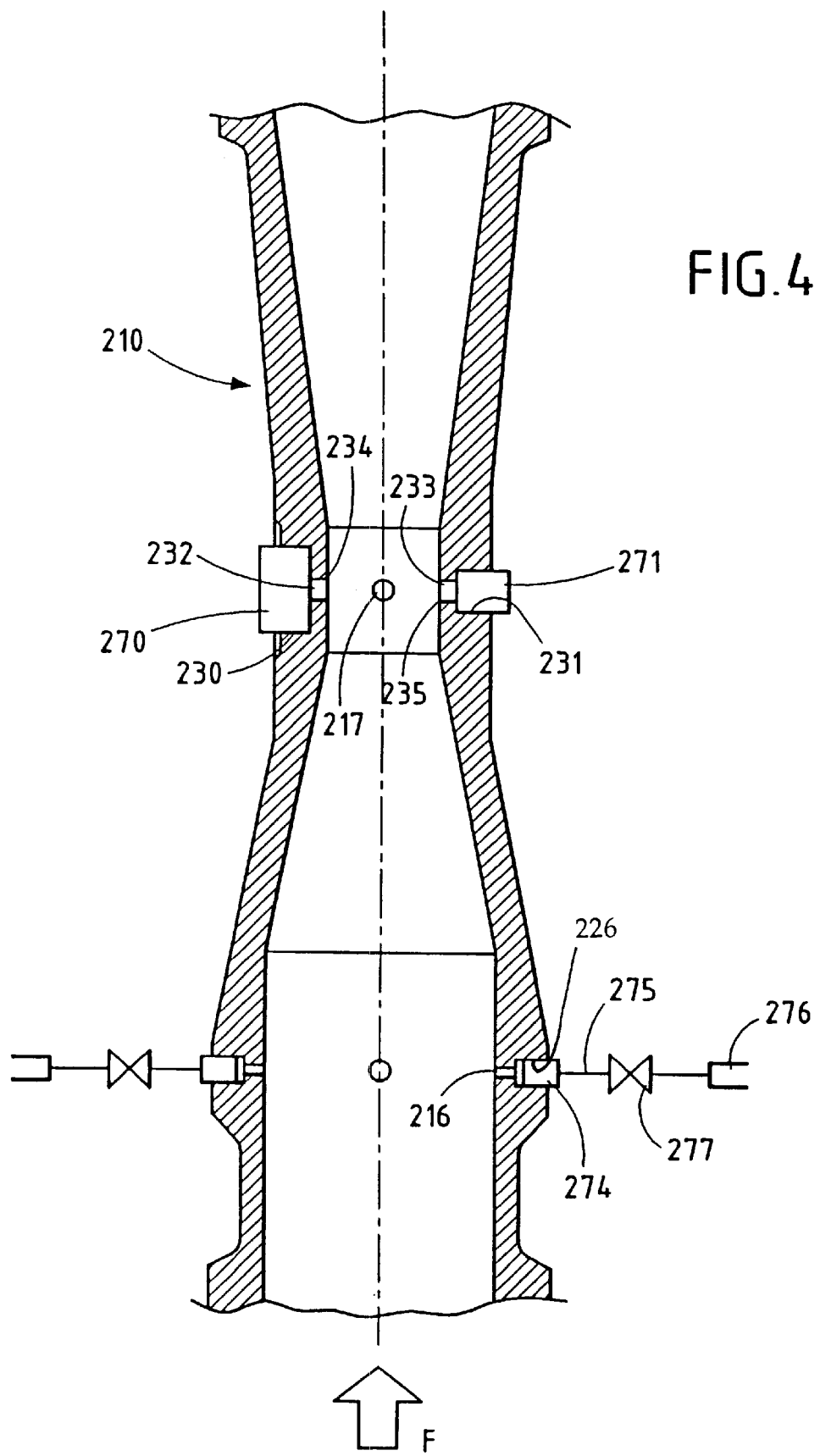
FIG. 4 is a diagram of a Venturi section as shown in FIGS. 2 and 3, and fitted for semi-periodic use.

Description with Reference to FIG. 4

The section view of FIG. 4 shows an advantageous way of using a device of the kind shown in FIG. 2. The principle consists in connecting a section of pipe which is adapted to taking measurements as described above to the production installation situated in the vicinity of a well head but does not include any measurement means proper (sensors and associated processor means). Such measurement section is permanently mounted on the main pipe connected to the well head, and valves are provided in the main pipe between itself and the measurement section so that when a measurement is to be performed, the well effluent can be diverted through the measurement section. Measurement means are assembled to the measurement section, thereby making up the device as shown in FIG. 2, only when a measurement is to be performed. This form of implementation, that can be referred to as "semi-periodic", makes it possible to perform periodic monitoring of production from a well under conditions that are advantageous for the user. Since the measurement section is already in place, the operations necessary to perform a measurement are restricted to assembling the sensors onto the measurement section and that can be done quickly and simply. In addition, the sensors which constitute the expensive and fragile portion of the device are not left exposed other than while performing monitoring operations. This is particularly advantageous for the gamma ray attenuation sensor which includes a radioisotope. Also, the sensors constitute equipment that is very lightweight (compared with the measurement section) and that does not require special transport means. Conversely, the measurement section is a piece of equipment that is robust and simple and that can be left permanently on a production site without great risk.

FIG. 4 is a diagram showing a measurement section of the type shown in FIG. 2, but while not performing measurement operations. Compared with FIGS. 2 and 3, corresponding elements are given the same reference numbers plus 100.

The measurement section is given overall reference 210. It is mounted in parallel with a production pipe connected to a well head in such a manner that the effluent can flow through the measurement section in the direction represented by arrow F when it is desired to take measurements. The pipes are provided for this purpose with valves (not shown). In appropriate manner, the measurement section is disposed vertically and the flow through the measurement section is upward, as indicated by arrow F.

The measurement section includes recesses for receiving the components of a gamma ray attenuation measuring device, said recesses passing through the wall of the measurement section at two diametrically opposite positions. A first recess, for the source, is formed in a housing 230 opening out into the outside wall of the measurement section 210, and of a smaller diameter housing 232 opening out in the inside wall, and similarly a second recess for the detector comprises a housing 231 opening out in the outside wall and a smaller diameter housing 233 opening out in the inside wall. The housings 230 to 233 are made in appropriate manner respectively like the housing 130 to 133 described in detail with reference to FIG. 3. Similarly, the housings 232 and 233 receive windows 234 and 235 made in appropriate manner like the elements 134 and 135 shown in FIG. 3 so there is no need to describe them again. It is merely recalled that each of the elements 134 and 135 is designed to have low gamma ray attenuation, and has sealing means associated therewith, and in a variant the two elements may be formed by separate portions of a single annular part provided with appropriate sealing means. The elements 234 and 235 are also protected by respective plugs 270 and 271 screwed into the housings 230 and 231. During a measurement operation, the plugs are unscrewed and the source block and the detector block elements described with reference to FIGS. 2 and 3 are screwed into the housings 230 and 231.

For measuring pressure in the flow, the measurement section shown includes pressure takeoff orifices 216 and 217 analogous to the orifices 116 and 117 of FIG. 2. A threaded housing 226 connects each housing to the outside of the measurement section. A connector 274 is screwed into the housing and is itself connected, as shown diagrammatically in FIG. 4, to a hydraulic line 275 provided with an end coupling 276 and including a valve 277 that is closed except when performing measurements. To perform a measurement, it thus suffices to connect the coupling 276 to the pressure sensor and to open the valve 277.

The principles explained above are also applicable to the case mentioned above in which the measurement section is used for gamma ray attenuation measurements only. Under such circumstances, there is no need to provide a Venturi in the measurement section, nor is there any need to provide pressure takeoff orifices for measuring the pressure drop due to the Venturi. Under such circumstances, the measurement section may be of constant diameter and need only comprise the "windows" presenting low gamma ray attenuation and the elements associated therewith, as described above.

We claim:

1. A measurement device for characterizing an oil effluent formed by a multiphase fluid mixture which may contain water, oil, and gas, the device comprising:
    a flow section including a Venturi;
    pressure sensors fixed to said flow section, said pressure sensors measuring the pressure drop that results from the flow passing through the Venturi;
    a gamma ray sensor fixed to said flow section, said gamma ray sensor measuring the attenuation of gamma rays passing through the effluent at the throat of the Venturi, said sensor comprising:
        a gadolinium 153 source emitting gamma rays through the effluent at a first energy level of about 100 keV and at a second energy level of about 40 keV; and
        and a detector detecting the gamma rays, after transmission through the effluent such that:
            the detected attenuation, A, of said first energy level of about 100 keV is an indicator of the density, $\rho_m$, of said multiphase fluid mixture according to the following relationship: $A = D_V \cdot v_m \cdot \rho_m$; where $D_V$ is the distance traveled by the gamma rays at 100 keV through the multiphase fluid mixture, and $v_m$ is the mass attenuation coefficient of the multiphase fluid mixture;
            the detected attenuation of said second energy level is sensitive to the water content of said fluid mixture.

2. A measurement device according to claim 1, including means for modifying the distance between the gadolinium source and the effluent to be characterized.

3. A method of characterizing an oil borehole effluent, formed by a multiphase fluid mixture which may contain water, oil, and gas, comprising the steps of:
    (i) causing the effluent to pass through a flow section including a Venturi;
    (ii) measuring the pressure drop that results from the flow through the Venturi by means of pressure sensors fixed to the flow section;
    (iii) emitting gamma rays at a first energy level of about 100 keV and at a second energy level of about 40 keV into the throat of the Venturi from a gamma ray source comprising a gadolinium 153 source;
    (iv) detecting the gamma rays at the first and second energies after transmission through the effluent with a detector fixed to the flow section and separated from the gamma ray source;
    (v) measuring the attenuation of gamma rays at 100 keV after transmission through the effluent;
    (vi) determining the density, $\rho_m$, of the mixture by the measurement of 100 keV attenuation, A, according to the following relationship:

$$A = D_V \cdot v_m \cdot \rho_m$$

where $D_V$ is the distance traveled through the fluid mixture by the gamma rays at 100 keV, and $v_m$ is the mass attenuation coefficient of the multiphase fluid mixture;
    (vii) measuring the attenuation of gamma rays at 40 keV after transmission through the effluent;
    (viii) determining the water content of the fluid mixture by the measurement of 40 keV attenuation;
    (ix) characterizing the effluent on the basis of determined density and water content of the mixture.

4. A method as claimed in claim 3 further, comprising the steps of making multiple measurements over a period of time and further including the step of modifying the separation of the gamma ray source and detector between measurements.

* * * * *